(12) United States Patent
Carr

(10) Patent No.: US 6,280,960 B1
(45) Date of Patent: Aug. 28, 2001

(54) OPTICAL DETECTION AND ANALYSIS OF SUB-MICRON PARTICLES

(76) Inventor: Robert Carr, Wayside, Thorneydown Road, Winterbourne Gunner, Wiltshire SP4 6LN (GB)

(*) Notice: Subject to any disclaimer, the term of this patent is extended or adjusted under 35 U.S.C. 154(b) by 0 days.

(21) Appl. No.: 09/308,049

(22) PCT Filed: Jun. 1, 1998

(86) PCT No.: PCT/GB98/01591

§ 371 Date: May 13, 1999

§ 102(e) Date: May 13, 1999

(87) PCT Pub. No.: WO98/57148

PCT Pub. Date: Dec. 17, 1998

(30) Foreign Application Priority Data

Jun. 13, 1997 (GB) .................................. 9712202

(51) Int. Cl.⁷ .................................. G01N 33/543
(52) U.S. Cl. .................. 435/7.2; 356/317; 356/318; 356/335; 356/336; 356/244; 356/246; 422/55; 422/68.1; 422/82.05; 422/82.08; 422/82.11; 435/287.1; 435/287.2; 435/287.9; 435/288.7; 435/808; 436/164; 436/165; 436/172; 436/518; 436/524; 436/525; 436/805
(58) Field of Search .................. 356/317, 318, 356/335, 336, 244, 246; 422/55, 68.1, 82.05, 82.08, 82.11; 435/7.2, 287.1, 287.2, 287.9, 288.7, 808; 436/164, 165, 172, 518, 524, 525, 805

(56) References Cited

U.S. PATENT DOCUMENTS

| 3,695,765 | 10/1972 | Boi et al. . |
| 3,975,084 | 8/1976 | Block . |
| 4,979,821 | * 12/1990 | Schutt et al. .................. 356/246 |
| 5,362,653 | 11/1994 | Carr et al. . |
| 5,478,755 | 12/1995 | Attridge et al. . |

FOREIGN PATENT DOCUMENTS

| 0 535 611 | 4/1993 | (EP) . |
| 0 575 132 | 12/1993 | (EP) . |
| 0 677 734 | 10/1995 | (EP) . |
| 90/11525 | * 10/1990 | (WO) . |

OTHER PUBLICATIONS

Y–K Kim et al., "Scanning Plasmon Optical Microscope", Appl. Phys. Lett. 66 (25), Jun. 19, 1995, pp. 3407–3409.

* cited by examiner

*Primary Examiner*—Christopher L. Chin
(74) *Attorney, Agent, or Firm*—Young & Thompson

(57) ABSTRACT

Method and apparatus for the single particle detection of submicron structures such as biological molecules and viruses utilises and optically transparent substrate coated with a thin film of metal illuminated with an optical beam incident at or close to critical or SPR angle wherein part of the beam propagates along the metal surface defining a measurement zone from which submicron particles contained in a sample placed in contact with the metal film scatter light which can be detected in the far field by conventional photodetection systems. The apparatus can be configured in a flow cytometric of optical microscope configuration.

18 Claims, 2 Drawing Sheets

OPTICAL DETECTION AND ANALYSIS OF SUB-MICRON PARTICLES

The present invention relates to the optical detection and analysis of particulates of nanometre, sub-micron or micron dimensions and in particular to particles of biological origin such as macromolecules, macromolecular assemblies, virus particles, microbial or animal cells or cell organelles.

A large number of principles and techniques exist by which particles can be analysed in terms of their number, size, shape, composition and motion.

Historically, the observation and charaterisation of particles lies in the domain of microscopy in which highly magnified images of particles are generated through the use of high powered lensed systems and which can be seen directly by eye or can be captured by camera for subsequent interpretation by the operator or by an image analysis system.

There are many types of microscope systems capable of characterising the particle in terms of its interaction with the incident illumination. For instance, the particle may selectively absorb certain wavelengths of the light such as in differential absorption, the technique most common in conventional transmission microscopy. Other microscopical variants exist which selectively monitor specific wavelengths generated by the particle when illuminated by the incident illumination, such as fluorescent microscopy which is useful in reducing background interference and which can be used to identify specific structures through the use of fluorescent labels. Yet other microscopical techniques utilise the way in which the particle induces a phase shift in the incident light, such as phase contrast or interference microscopy. Other microscope techniques, such as epiluminescent microscopy, employ light scattering at high angles to allow low contrast particles to be visualised against a low background. Other similar versions of this technique are used in microscopy, of which the most common is referred to as dark field microscopy. In this case, the sample is illuminated by a high numerical aperture source and the central portion of the illuminating cone is blocked from entering the detection objective by an optical stop so that the particle is illuminated at an oblique angle only.

Methods of illumination vary greatly and in certain circumstances the sample (typically and aqueous suspension of particles) can be placed on a transparent (typically glass or silica) optical substrate which is illuminated by a suitably defined and collimated optical beam at a certain angle called the critical angle at which the incident light is refracted along the plane of the optical element on which the liquid sample is place. A small portion of the beam, called the evanescent wave, propagates a small liquid sample is placed. A small portion of the beam, called the evanescent wave, propagates a small distance into the sample phase above the optical substrate and particles entering this evanescent region act to scatter some of this otherwise non-radiative field. The light coupled out (i.e. scattered by the particle with the evanescent field) can then be detected in the far field either by eye or by a suitable detector situated normal or at high angle to the plane of the surface. When employed in a microscope configuration this technique is referred to as evanescent field microscopy and relies on the principle of frustrated total internal reflection Other techniques, such as confocal microscopy, benefit from the specific properties exhibited by light sources such as lasers in which the light can be highly collimated, monochromatic, coherent and very intense.

All the above techniques suffer, however, from being limited by the classical diffraction or Rayleigh limit which restricts, in practice, the useful resolving power of optical microscopes to approximately $\lambda/2$ which precludes the imaging of particles of less than 0.2–0.5 $\mu$m diameter.

Numerous non-imaging methods exist for the optical analysis of suspensions $\mu$m or sum-$\mu$m particles or solutions of nm scale particles such as biological molecules or macromolecules. Many such techniques monitor the interaction between biological molecules and in order to define a region within such interactions can be specifically detected within minimal interference from other species in the bulk of the solution phase, such analyses are frequently carried out at the interface of an optical waveguide or fibre optic structure onto the surface of which have been immobilised biological capture molecules such as antibodies, specific for the target analyte. In conventional waveguide or fibre optic systems use is made of the changes in the refractive index properties at the surface interface following binding of specific biological molecules in the surface associated evanescent field region of the optical structure. This field extends, however, only some 100–200 nm into the bulk solution phase and is accordingly limited in its ability to monitor weak interactions involving limited numbers of molecular interactions. Such a method is disclosed in DE 4307042 (930305), in which a single or multilayer of receptor molecules are deposited on and evanescent waveguide sensor device and which is capable of sensing and quantifying various chemical and biochemical species in solution. A similar method is disclosed in WO 9005295 claiming priority of SE 884075 (881110) in which a wedge shaped prism is used to allow light reflected at different angles off the underside of the optical sensor element to be imaged and analysed to quantify specific species in solution. Similarly, EP677735 claiming priority of U.S. Pat. No. 228233 (940415) describes and optical resonator cavity in which light is reflected from a total internal reflector cavity in contact with a solution components of which interact with the evanescent field within the TIR allowing quantification of species in the solution These techniques are characterised by their reliance on the analysis of light which is reflected from the underside of a sensing element surface.

The ability to follow such low numbers of interactions or binding events can, however, be significantly enhanced, by one or two orders of magnitude, by employing Surface Plasmon Resonance techniques in which the surface of the optical waveguide structure is coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed. Thus WO 9005305 claiming priority of SE884074 (881110) describes the use of a metal film deposited on one side of a block unit of optical instrumentation, one multi-functionalised side of which is in contact with a solution of reagents or samples to be measured, the other side is illuminated by an optical beam within the block unit of optical instrumentation caused to reflect off the metal surface at an angle such that reflectance is modified by selective binding of ligands on the functionalised surface.

Measurement of the reflected beam can be correlated to concentrations of specific species binding to the functionalised sensor surface.

Similarly EP 341927 claiming priority of GB881154 (880510) describes a biological or biochemical testing sensor comprising a surface plasmon resonance (SPR) sensor and a sample-antibody surface arranged to influence resonance characteristics. The SPR sensor comprises a metallised glass slide onto the glass-metal interface of which is directed a beam of light at an angle at which surface plasmons are induced to resonate in the metal film. Changes in the resonance angle on binding of analyte are determined by measuring the intensity or angle of the light internally reflected from the metal-glass interface.

As with the evanescent techniques described above, these techniques are characterised by their reliance on measuring the intensity of light reflected from the surface or changes in the resonance angle on binding of specific sample components.

Furthermore, such non-imaging reflectance techniques monitor only the binding of relatively large numbers of macromolecules through measurement of changes in the amount or position of the reflected light. Such reflectance techniques cannot be used to locate, visualise, detect or count the presence of individual macromolecules or very sub-$\mu$m particulates because the optical effect of interaction of individual nm or very sub-$\mu$m scales structures with an optical beam is too small to be distinguished from the high levels of light reflected from the metal surface though images of the interaction of surfaces of large (e.g. 1–50 $\mu$m cellular) structures can be obtained by observing the spatial distribution of light reflected from the underside of the metal film if they are sufficiently large to be able to distinguish from the main reflected beam.

If generation of images of individual particles are not required, for instance when it is only necessary to determine the presence or otherwise of particles and to estimate their size, size distribution, number etc., then other principles in which light scattering phenomena predominate may be used. Such methods rely on the measurement of the amplitude of optical signal generated by the interaction of particles with suitably intense and focused beams of light (typically from laser sources), each particle passing through the optical measurement zone in which the interrogating beam is caused to pass, signals generated by the interaction of the particle with the optical beam being detected by suitable photosensitive devices such as photomultiplier tubes, photodiodes, CCDs and the like.

Such instruments are referred to as particle detectors or particle counters and are used widely in a variety of industrial and scientific applications. One such technique, known as flow cytometry, allows particles in a concentrated suspension, to be addressed on an individual basis by diluting the sample through adding it slowly to a rapidly flowing hydrodynamic sheath of substantially particle free liquid, the outpout of which is directed by a finely adjusted nozzle to flow accurately through a concisely focused measurement volume. By measuring the scattered light intensity and where applicable, the fluorescence wavelength generated by the interaction of the particle with a suitably focused and intense optical sources particles as small as 0.2 $\mu$m can be quantified and various optical parameters relating to their size and differential absorption or fluorescence characteristics can determined.

The analysis of light scattered by a particle passing through a finely focussed light beam has the merit of simplicity but the technique suffers from a drawback associated with the particles "clipping" the edge of the illuminating beam leading to ambiguity in analysis of small particles passing through the center of the beam compared to larger particles passing off axis through the edge of the beam, both particles capable of scattering, in many instances, the same amount of light to the detector. This problem has been overcome in one known arrangement U.S. Pat. No. 4,927,268 claiming priority of GB 8621426 (860905) which discloses an optical arrangement in which two wavelengths of light propagating through a single fibre optic to ensure common alignment one of which is used can be focused to a smaller diameter beam concentric to other to differentiate the centre of a scattering volume to aid accuracy of analysis.

Below a certain particle size limit, however, the signal generated by the interaction of the particle with the interrogating beam of light is insufficient for it to be distinguished from the background inherent in such optical light scattering instrument configurations. Increasing the intensity of the interrogating optical beam acts merely to increase the intensity of background as well as the signal generated by the particle. To determine the presence of such very sub-micron particles it is normally usual to employ higher resolution non-optical techniques such as electron microscopy but which suffer from significantly higher complexity and cost.

There is therefore a need for a simple and low cost optical particle detection system capable of detecting the presence of particles substantially below ¼ of the wavelength of illuminating radiation on an individual basis without the need for expensive, high powered and hazardous optical sources, which is compatible with existing optical microscopes and particle detection apparatus, which is simple to use and operate and which is capable of furnishing information, such as particle size, size distribution, number and other optical parameters on suspensions of particles of mixed characteristics in frequently complex background.

The present invention is based on the unexpected finding that when a small volume of a suspension of sub-micron particulates, exemplified by biological virus particles, are placed on a metallised optical element comprising an optically transparent (glass or silica) surface coated with a thin (10's nm) film of metal, for example chrome, silver or gold, and which is illuminated by a beam of light incident on the metal/glass interface at or close to the critical or SPR angle for that optical structure when in contact with the particle-bearing medium, individual sub-micron particles within the contacting fluid and in close proximity to the point at which the optical beam is incident on the metal film are found to scatter sufficient amounts of light so as to be individually discernible through a conventional microscope objective/lens combination, by eye or by a suitable photodetector such as a photon multiplier tube, solid state photodiode, CCD camera or other photosensitive device placed in an image plane in the far field and normal or at high angle to the plane of the otherwise non-radiative metallised surface. The particles capable of being thus individually detected are of a dimension such that they would not otherwise have been detectable by convention optical transmission, dark-field, phase contrast or evanescent field microscopic techniques.

Thus, according to the present invention there is provided a method and apparatus for the individual optical detection and characterisation of small (relative to the wavelength of light being used for illumination) particles suspended in a transparent fluid or gas medium for the purposes of determining particle characteristics such as size, size distribution, number concentration, shape or other optical charactiristics such as fluorescence, polarisation, phase modulating properties, etc. wherein the particle suspension is contacted with one side of an optical element comprising a transparent optical substrate such as a glass or solica slide or prism the surface of which in contact with the particulate suspension has been coated with a thin film of metal such that when illuminated by a suitably intense and focused beam of light caused to be obliquely incident to the metal/glass interface at or close to critical or SPR angle, such that the beam of light is cause, by refraction, to propagate along or close to the plane of the metallised surface of the optical element, those particles in the vicinity of the illuminated region of the metal surface or the propagating beam in contact with the particle bearing fluid cause detectable amounts of light to be scattered or emitted in to the far field for subsequent visualisation by eye or for detection and analysis by a suitable photodetector placed in an image plane in the far field at normal or high angle to the plane of the metallised surface. Fluorescence emitted by, or light scattered from, the particles is seen, by eye or by suitable detectors, as a point of light arising from each particle in the measurement region, the amplitude of signal from each of which can be indicative of various optical properties of the particles as well as indicating its presence size, motion and number concentration, fluorescence, etc. all parameters of which can be quantified, if desirable, by suitable signal processing or image analysis instrumentation.

In accordance with the invention, microscope optics and instrumentation can be used to allow particles so small as to be otherwise undetectable by conventional optical microscopy techniques to be individually detected for the purposes of determination of particle presence, size, particle size distribution, concentration, number, fluorescent attributes, whether inherent or through the addition of fluorescent labels for measurement of specific parameters associated with the particle composition, polarisation modifying properties, phase modulating properties or any other parameter normally addressable by optical methods of analysis.

In the particular case where the present method and associated apparatus could be used in conjunction with a non-microscopical application, such as in the case of a particle counting apparatus for the purposes of determining particle count as a function of size class, the particle suspension can be caused to flow over the surface of the optical element such that particulate suspensions that would otherwise be so dilute as to contain too few particles with the measurement volume for statistically accurate estimation of particle presence or number concentration or size distribution to be made, an increased volume of the particle-containing medium can be caused to flow over the detection region thereby increasing the number of particles capable of being accurately detected and alalysed. For particle counting and analysis on such larger volumes the present method may be employed in an optical particle measurement and analysis system exemplified by those instruments known as flow cytometers in which a suspension of particles is caused to pass through an optical measurement region by introducing, via a nozzle, the particulate-bearing sample into a stream of substantially particle free fluid moving at a higher velocity, known as a hydrodynamic sheath, such that the particle-bearing sample is diluted to the point where particles pass through the optical measurement region on an individual basis and the direction of the flow of particle-bearing sample can be finely adjusted to be optimally aligned with the optical measurement region. One type of flow cytometer employs what is known as a jet-on-an-open-surface (JOOS) configuration in which the sample bearing hydrodynamic sheath flow is played onto a flat, optically transparent surface such that the position of the sample stream can be finely adjusted through adjustment of the nozzle position and flow velocity to be more accurately placed at the waist of the interrogating optical beam. In accordance with the invention the use of a metallised optical surface, as described herein, advantageously allows smaller particles than would otherwise be optically detectable to be visualised in such a system by virtue of the enhancement of visibility afforded by the presence of the metal film.

The process of the invention may thus be used to determine particle presence, size, particle size distribution, concentration, number, fluorescent attributes, whether inherent or through the addition of fluorescent labels for measurement of specific parameters associated with the particle composition, polarisation modifying properties, phase modulating properties or any other parameter normally addressable by optical methods of analysis but which is particularly useful for carrying out such analyses on particles that are so small as to be otherwise undetectable on an individual basis by optical systems incorporating bulk lens configurations such as conventional microscopes, flow cytometers or other optical particle measurement instruments.

In this regard it has been found that the present invention allows sub-micron particles such as unlabelled viruses in solution to be directly visualised and counted on an individual basis through the use of optical sources of moderate power such as solid state laser devices of mW output. The present invention, by virtue of its sensitivity to detection of particle-associated events close to a surface, further allow the interaction of sub-micron particles with surface coatings and functionalised layers to be individually monitored and analysed in time. Such events may include the interaction of discrete virus particles with a coating on the optical element specifically designed to substantially reproduce the properties exhibited by a cell surface for the purposes of investigating virus-cell wall infection events.

Similarly, in accordance with the invention the adhesion of sub-micron regions of cell walls and regions thereof with surfaces, chemically or biochemically modified or otherwise, may be monitored at resolutions and sensitivities exceeding those afforded by conventional optical microscopic techniques. Advantageously, such events can be monitored in real time and in an aqueous environment unlike those lyophilised conditions necessary for visualisation of such interactions by electron microscopy.

The range of the types of particle which can be individually seen by the process of the invention is also varied and broad. The use of the metallised optical element herein described, by virtue of its ability to generate detectable optical signals from sub-micron particulates, allows the process of the invention to be applied to the estimation of contaminant levels in process or industrial fluids and liquids which are desired to be contaminant free, the detection of virus particles and other sub-micron biological entities in biological, environmental, biotechnological and clinical samples, such as blood and urine and other body fluids, purification media, pharmaceutical preparations, and the like. Other particulates in solution or suspended in a gas phase that may be individually detected, counted and characterised in accordance with the invention include contamination organic or inorganic particles in otherwise particle free fluids, smoke or other combustion product particles in gases, contaminants in oils, micro-emulsion (oil in water or water in oil) droplets, liposomes and vesicles, micelles sub-microscopic cells such as mycoplasmas, colloids of natural or industrial origin, or any suspension, colloidal fluid or preparation in which light scattering centres exist and which are too small too be analysed by conventional optical instrumentation. It will, of course, be appreciated that the process of the invention allows any particulate capable of scattering or modifying radiation incident upon it and which can be distinguished from the background by a suitable detector to be individually detected and analysed.

It will be further appreciated that the process of the invention is applicable to the analysis of individual macro-molecules and macromolecular constructs which, through labelling with a suitable optical amplifier or fluorescent label capable allowing them to be distinguished from the background, would not otherwise be detectable on an individual basis using conventional optically based particle characterising instrumentation.

The use of the metallised optical element illuminated with a suitable optical source as described herein is particularly advantageous in the readily available light sources of modest power such as low cost gas, diode or solid state lasers can be used in conjunction with conventional detection optics and electronic photosensitive devices to detect particles which normally would only be capable of being individually visualised by very much more sophisticated and complex techniques such as electron microscopy.

The invention will now be described in more detail by way of example with particular reference to the accompanying schematic drawings of which;

Figure 1:
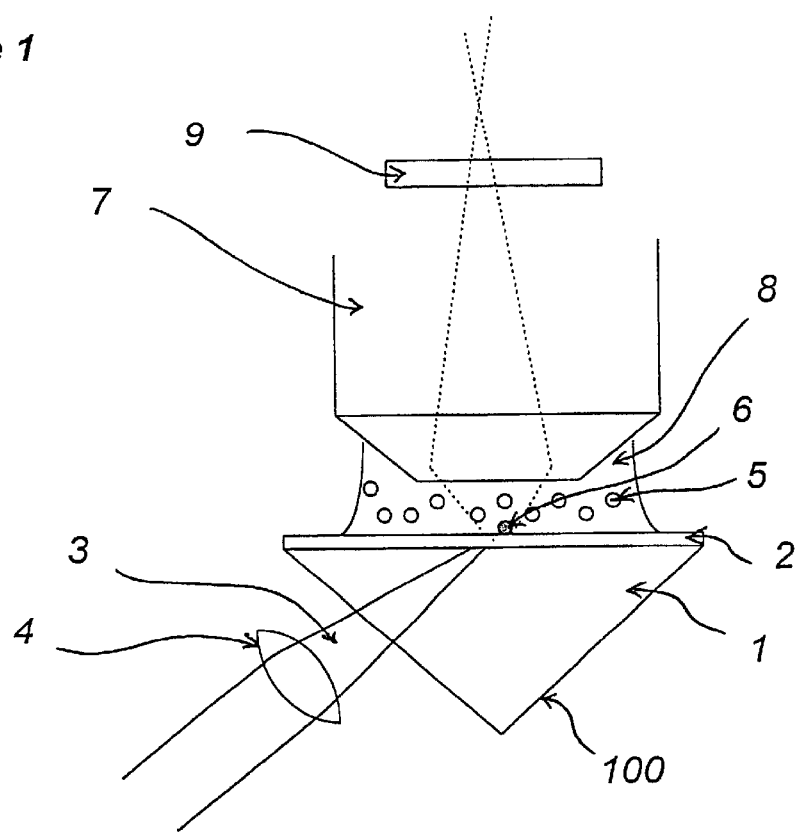
FIG. 1 illustrates apparatus according to the invention for the detection of sub-$\lambda$ particles such as viruses suspended in an aqueous fluid.

Referring to FIG. 1, an instrument element 100 consists of an optically transparent substrate 1, typically a glass or silica prism, onto which is deposited a thin film of metal 2, typically less than 50 nm depth of gold, silver aluminum or chrome deposited by any suitable sputtering, vapour phase, electrochemical or other means. A light beam of suitable collimation, intensity, polarisation and wavelength or wavelength range 3 is focused by lens 4 to be incident on the glass/metal interface at or close to the critical or SPR angle for that optical configuration such that when a sample of liquid 8 containing a suspension of particles 5 is placed onto the surface of the metal film 2, those particles 6, in close proximity to the point at which the optical beam is incident on and thus propagates along or close to the direction of the plane of the metal film, individually act to scatter light which can be detected in the far field by a suitably aligned and focused lens arrangement 7 such as a microscope objective, which could be an immersion lens, and associated lenses to be subsequently observed by eye or analysed using a photosensitive device and suitable signal processing or image analysis instrumentation.

It will of course be understood that besides the simple observation of light scattered by particles 6, other optical consequences of their coming into close proximity to the region of the metal/glass interface illuminated by the optical bean 3 may be observed and analysed. Thus, if the particle population 5 is comprised entirely or partially of particles which are inherently fluorescent or have been specifically labelled through the use of selected fluorescent labels, those particles which fluoresce on coming into close proximity to the region of the metal/glass interface illuminated by an exciting optical beam 3, may be specifically observed through the lens assembly 7 if the image is first filtered by a suitable fluorescence filter assembly 9.

It will be further understood that the use of several different fluorescence filters will allow multiple wavelengths to be separately analysed extending the information that can be obtained about a multiply stained particle suspension under view.

It will be further understood that the detection lens assembly 7 could, if required, be placed on the opposite side of the optical element 100, if the apex of the prism were to be removed or modified in shape to present an optically flat surface through which the scattered light of fluorescence from the particles could then be detected, the metal film being sufficient thin at normal or high detection angles to allow sufficient amounts of radiation to pass through it to allow observation and analysis of the particle suspension.

Figure 2:
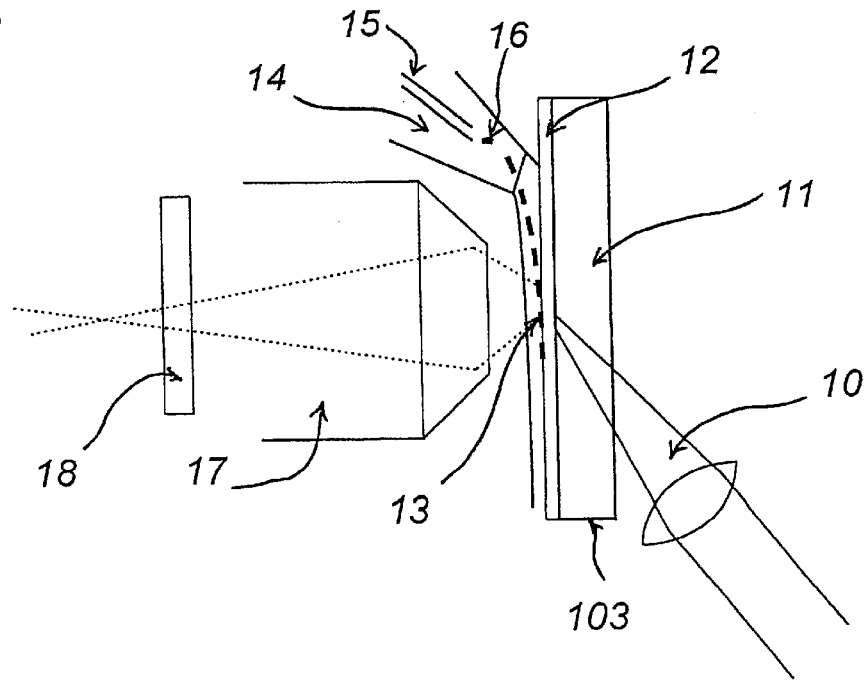
FIG. 2 illustrates one use of the invention for application in a flow cytomnetric configuration

In FIG. 2 is shown an alternative apparatus for use in a flow cytometric configuration of the jet-on-an-open-surface type. Optical element 103, consists of an optically transparent planar substrate 11, typically glass or silica onto which is deposited a thin film of metal 12, typically less than 50 nm depth of gold, silver, aluminum or chrome deposited by any suitable means. A light beam of suitable collimation and wavelength 10 is caused to be incident on the glass/metal interface of optical element 103 at or close to the critical or SPR angle for that optical configuration. When a hydrodynamically focused stream of fluid 13 emanating from a nozzle 14 and containing a stream of particles 13 introduced into the hydrodynamics sheath fluid by tube 15 is passed through the region at which the optical beam is incident on the glass/metal interface of optical element 103, particles directed, by fine adjustment of nozzle 14, to flow in close proximity to this region will either scatter light or be induced to fluoresce, the optical radiation of which is detected, through use of lens system 17 containing a fluorescent filter assembly 18 if required, by a suitable photosensitive detector and associated signal processing electronics capable of measuring the optical signal generated by the separate particles at a rate which allows particles to be analysed individually and sequentially at high rates, typically hundreds or thousands per second. The lens assembly 17 can be designed and constructed such that one or more of a variety of angles of scattered light can be selected from the scattered radiation or fluorescence emanating from the particle.

It will understood that the detection lens assembly 17, or an additional lens and detector assembly could, if required, be placed on the opposite side of the optical element 103, through which the scattered light or fluorescence form the particles could then be detected, the metal film being sufficiently thin at normal or high detection angles to allow sufficient amounts of radiation to pass through it to allow observation and analysis of the particle suspension.

Figure 3:
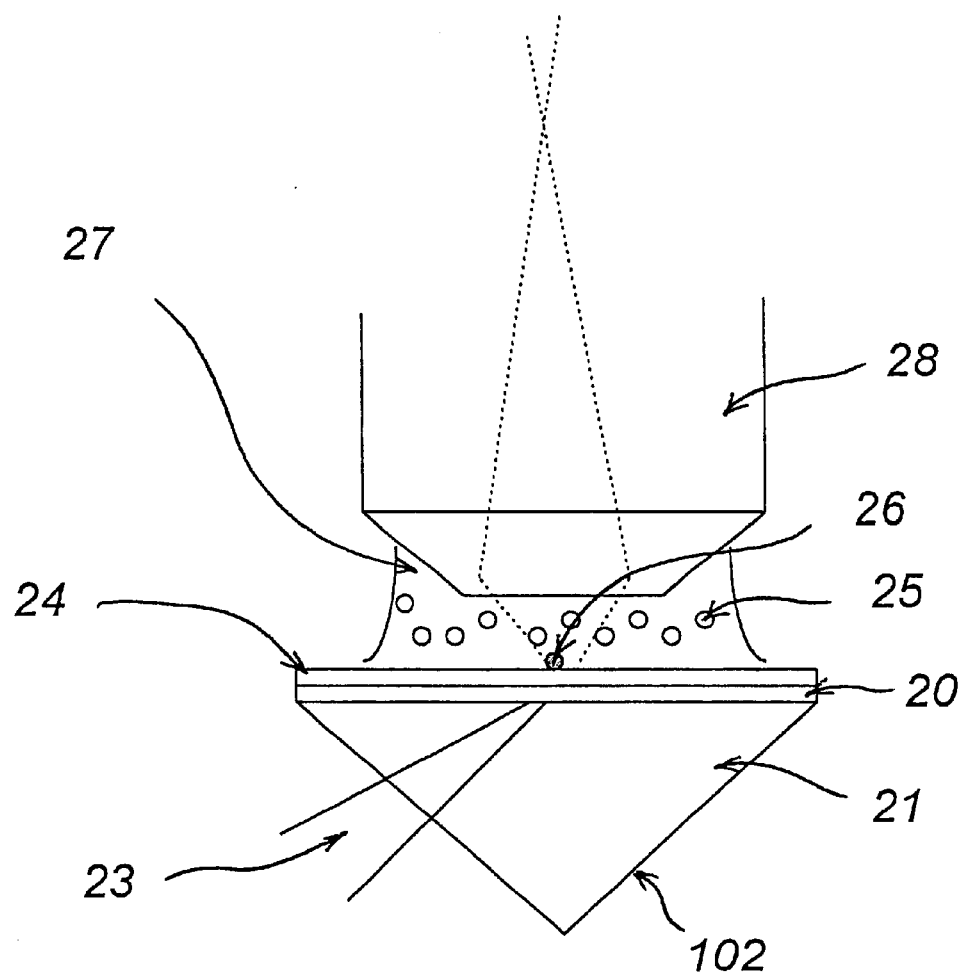
FIG. 3 illustrates the use of the apparatus for studying the interaction of particles with a functional layer deposited on the optical element.

In FIG. 3 is shown an alternative configuration for the detection of interaction of particles with a functional surface comprising an instrument element 102 consisting of an optically transparent planar or prism substrate 21, typically glass or silica, onto which is deposited a thin film of metal 20, typically less than 50 nm depth of gold, silver, aluminum or chrome deposited by any suitable means. A functional layer 24 can be deposited onto the metal film 20 which may comprise a polymeric or biological material which substantially replicates the properties exhibited by a natural cell membrane or wall surface and from which the interaction of particles 26 in a liquid 27, which may, for instance, be inefective virus particles, can be obtained information about the rate, number and behaviour of binding events between the particles and the functional surface. Alternatively, the functional layer may comprise a chemically or biochemically modified layer onto which have been attached chemical or biological molecular moieties such as antibodies or other selective ligand binding structures which exhibit a specific affinity for target molecular or particulate structures, 26 the presence and number or behaviour of which is required to be established in the sample 27. A light beam of suitable collimation and wavelength 23 is caused to be incident on the glass/metal interface at or close to the critical or SPR angle for that optical configuration such that when the sample of liquid 27 containing particles 25 is placed onto the surface of the metal film 20, those particles 26, in close proximity to the point at which the optical beam is incident on the underside of the non-radiative metal film and which have an affinity for and can bind to functional layer 24, act to scatter light changes in the intensity of which on binding to the functional surface can be detected in the far field by a suitably aligned and focused lens arrangement 28 (such as an immersion microscope objective) to be subsequently observed by eye or analysed using a photosensitive device and suitable signal processing or image analysis instrumentation.

As in the other embodiments described above, it is of course obvious that besides the simple observation of changes in light scattered by particles 26, other optical consequences of their coming into close proximity to the region of the metal/glass interface illuminated by the optical beam 23 may be observed and analysed. Thus, if the particle population 25 is comprised entirely or partially of particles which are inherently fluorescent or have been specifically labelled through the use of selected fluorescent labels, those particles which fluorescence on coming into close proximity to the region of the metal/glass interface illuminated by the optical beam 23, may be specifically observed through the lens assembly 28 if the image is first filtered by a suitable fluorescence filter. Similarly, rotation of the polarisation of the incident beam by the particles can be measured in this invention.

It will be further understood that the use of several different fluorescence filters will allow multiple wavelengths to be separately analysed extending the information that can be obtained about a multiply stained particle suspension under view.

It will be further understood that the detection lens assembly 28 could, if required, be placed on the opposite side of the optical element 102, through which the scattered light or fluorescence form the particles could then be detected the metal film being sufficiently thin at normal or high detection angles to allow sufficient amounts of radiation to pass through it to allow observation and analysis of the particle suspension.

In the preferred embodiment, the optical element is a silica quartz planar substrate onto which has been deposited by a sputtering method, an approximately 40–50 nm thick layer of gold the surface first having been thinly coated with a 2 nm layer of chrome to assist adhesion of the gold. The optical element is illuminated at grazing incidence by a laser beam of modest power, for example 50 mW and suitable wavelength, for instance 488 nm. A drop of a biological sample such as a throat swab diluted in phosphate buffered saline containing a population of unlabelled refractile virus particles of clinical significance (such as adenoviruses) is placed on the optical element surface and the light the virus particles scatter as they move under Brownian motion in the vicinity of the point at which the optical beam is incident on the metallised optical element is observed by eye down a conventional microscope fitted with a ×40 immersion objective. Images of the virus can, of course, be captured on film or on video recording by suitable instrumentation for subsequent viewing and analysis. The presence and number concentration of virus particles in the sample can be determined from the intensify of light they scatter (light scattering in this size region being a strong function, for instance radius[6], of their size) of from counting the number of points of light of intensity associated with a particle size per unit volume in the sample for any given illumination intensity.

It should be noted that the invention is not confined to the case where samples are in solution. Where they are however, the solvent need not be water or event liquid but the solution may take the form of any form known to physical chemistry in which particles can be optically differentiated from their surrounding environment for analytical purposes. Furthermore, it should be clear that the process of the invention can be applied to situations in which the particulates to be detected and individually visualised are acted on by other physical forces, such as electrical or acoustic fields, so as to, for instance, induce physical motion or separation from other constituents in the sample.

Besides the embodiments of the method and the apparatus described above the invention can be used in a variety of other configurations and for a variety of other purposes. Thus, besides the incorporation of the invention into a JOOS type flow cytometric configuration it could be incorporated into any other optical detection apparatus in which the interaction of very small particles with and optical field is measured. For instance, the invention could be incorporated into a scanning probe microscope, such as a scanning near-field microscope, as a means of visualising a surface and locating desirable or interesting features on that surface to assist in the efficient high resolution scanning and imaging of the surface by the scanning probe tip.

Similarly, the invention could be used to enhance the performance of and derive more information from other analytical techniques such as Surface Plasmon Resonance (SPR) techniques allowing SPR device surface features and areas of interest to be identified and spatially located. This would allow specific particulate-bearing regions of the SPR surface to be spectroscopically analysed instead of taking readings from a random or otherwise uncharacterised or undefined point on the measurement surface as is done presently.

It should also be noted that small particulates interacting with the optical field present at or close to the surface of the optical element described herein, can be subject to physical motive forces form the light itself, a phenomenon known as photophoresis. This ability to modify the physical motion of particles, for instance effectively trap them in a certain location by the pressure of light alone, could be used to advantage in the analysis and manipulation of particles in accordance with the invention.

Particular benefits which ensue from the process in accordance with the invention include the ability to directly and individually visualise sub-microscopic particles such as viruses and other particles in the 10–500 nm diameter range which have not had to be optically amplified by use of fluorophore or light scattering labels and which would not otherwise be detectable by conventional microscope instrumentation. Analytical resolution is greatly improved by the ability afforded by the invention to characterise and analyse on a particle-by-particle basis a population of particles that may be diverse in size and optical properties. The physical components from which the apparatus can be assembled are not complex or expensive and can be used by non-expert users. The apparatus lends itself to being retrospectively fitted to a range of existing optical analytic instrumentation and instrumentation designs to improve resolution and performance.

It should be understood that though this invention has been described by way of various examples a variety of modifications are possible without departing from the scope of the appended claims.

I claim:

1. A method for the optical detection and analysis of sub-micron particulates comprising the steps of:
   I. illuminating with radiation from a suitable optical source, an optically transparent substrate coated on one side with a thin layer of an optically opaque metal such that the optical beam is caused to be incident on the substrate-metal interface at or close to grazing incidence such that a portion of the incident optical beam propagates along the surface of the metal film or at an angle close to the plane of the metal film or at an angle at which surface plasmons are caused to be excited in the metal film such that a portion of the electromagnetic field associated with said beam propagates at least in part in the medium above the metal film to form a measurement zone;
   II. placing onto the surface of the metal film not in contact with the optical substrate a sample containing a population of particles of sub-micron dimensions such that particles enter the measurement zone;
   III. detecting, by a suitable lens and detector arrangement situated in a far field at normal or high angle to the plane of the metal film, the electromagnetic radiation individually scattered by or otherwise caused to emanate from the particle through its interaction with the electromagnetic field within the measurement zone for the purposes of analysis of particles in said sample.

2. A method according to claim 1 wherein said particles are analysed in terms of their number concentration, size, distribution, shape or motion.

3. A method according to claim 1 wherein said particles are analysed in terms of the intensity and wavelength of fluorescent or other non-scattered radiation they emit or are caused to emit by virtue of their interaction with the illuminating radiation.

4. A method according to claim 1 wherein said particles are analysed in terms of their polarisation or phase modulating properties.

5. A method according to claim 1 wherein said particles are caused to enter the measurement zone on an individual basis.

6. A method according to claim 1 wherein several particles are present in the measurement zone at any one time the optical from each of which can be differentiated to allow said particles to be individually characterised.

7. A method according to claim 1 wherein the particles in the sample are labelled with fluorescent molecules to allow them to be distinguished from other particles and background noise.

8. A method according to any preceding claim 1 wherein an additional functional layer with which particles in the sample will interact or bind is deposited onto the surface of the metal layer in contact with the sample in order to monitor the interaction of said particles with said functional layer.

9. A method according claim 8 wherein the functional layer deposited onto the metal layer in contact with the sample is biochemically modified or otherwise chemically modified so as to confer selectivity of binding of particles in the sample.

10. A method according to claim 8 wherein biological capture molecules such antibodies are immobilised the functional layer so as to bind specific particle types as a function of their molecular structural features.

11. A method according to claim 1 wherein interactions between particles in the sample can be detected and analysed.

12. A method according to claim 1 wherein particulate structures detectable by this technique are part of a larger supramacromolecular structure whose physical and chemical attributes and behaviour can be ascertained from observation of its constituent parts.

13. A method according to claim 12 wherein said large structure is a cell, animal cell wall, a biofilm, a polymeric layer or other structure.

14. Apparatus for optical detection and analysis of sub-micron particles, comprising an optically transparent substrate coated on one side with a thin layer of an optically opaque metal illuminated with a beam of optical radiation from a suitable optical source, such that the optical beam is caused to be incident on the substrate metal interface at or close to grazing incidence such that a portion of the incident optical beam propagates along the surface of the metal film or at an angle close to the plane of the metal film or at an angle a which surface plasmons are caused to be excited in the metal film such that a portion of the electromagnetic field associated with said beam propagates at least in part in the medium above the metal film to form a measurement zone; means of placing onto the surface of the metal film not in contact with the optical substrate a sample containing a population of particles of sub-micron dimensions such that particles enter the measurement zone; means of detecting, by a suitable lens and detector arrangement situated in a far field at normal or high angle to the plane of the metal film, the electromagnetic radiation individually scattered by or otherwise caused to emanate from the particle through its interaction with the electromagnetic field within the measurement zone.

15. Apparatus according to claim 14 wherein the optical source is a laser.

16. Apparatus according to claim 14 wherein the region comprising the optically transparent substrate is part of a larger assembly designed and constructed for purposes other than particle detection.

17. Apparatus according to claim 14 for incorporation into a conventional microscope configuration.

18. Apparatus according to claim 14 for incorporation into a flow cytometer instrument configuration.

* * * * *